(12) United States Patent
Lindenberg

(10) Patent No.: US 10,456,096 B2
(45) Date of Patent: Oct. 29, 2019

(54) METHOD AND APPARATUS FOR PROVIDING TWO DIGITAL PANORAMIC LAYER IMAGES

(71) Applicant: DENTSPLY SIRONA inc., York, PA (US)

(72) Inventor: Kai Lindenberg, Wersau (DE)

(73) Assignee: DENTSPLY SIRONA Inc., York, PA (US)

(*) Notice: Subject to any disclaimer, the term of this patent is extended or adjusted under 35 U.S.C. 154(b) by 229 days.

(21) Appl. No.: 15/528,152

(22) PCT Filed: Nov. 23, 2015

(86) PCT No.: PCT/EP2015/077308
§ 371 (c)(1),
(2) Date: May 19, 2017

(87) PCT Pub. No.: WO2016/079337
PCT Pub. Date: May 26, 2016

(65) Prior Publication Data
US 2017/0354388 A1 Dec. 14, 2017

(30) Foreign Application Priority Data

Nov. 21, 2014 (DE) .................. 10 2014 223 802

(51) Int. Cl.
*A61B 6/14* (2006.01)
*A61B 6/00* (2006.01)

(52) U.S. Cl.
CPC .............. *A61B 6/14* (2013.01); *A61B 6/4266* (2013.01)

(58) Field of Classification Search
CPC .......... A61B 6/032; A61B 6/14; A61B 6/4266; A61B 6/4233; A61B 6/463; A61B 6/469;
(Continued)

(56) References Cited

U.S. PATENT DOCUMENTS 8,045,772 B2  10/2011  Kosuge
8,891,845 B2  11/2014  Ogawa
(Continued)

FOREIGN PATENT DOCUMENTS

WO       2006127416 A2    11/2006

OTHER PUBLICATIONS

International Search Report dated Mar. 7, 2016.
(Continued)

*Primary Examiner* — Irakli Kiknadze
(74) *Attorney, Agent, or Firm* — Dentsply Sirona Inc.

(57) ABSTRACT

The invention relates to a method for providing a first and a second digital panoramic layer image optimized for a comparison, wherein the first and second panoramic layer images each have multiple projections detected and stored for them by means of at least one digital detector during an at least partial revolution of a recording unit around an object to be recorded, and the first and second panoramic layer images are each produced from the multiple projections in accordance with a computation code and by forming a panoramic layer. Differences between the first and second panoramic layer images are minimized by altering at least one parameter of the computation code for fresh production of the first and/or second panoramic layer image. In addition, the invention relates to a corresponding apparatus.

7 Claims, 1 Drawing Sheet

(58) Field of Classification Search
CPC ... A61B 6/5205; A61B 6/5241; A61B 6/4028; A61B 6/587; A61B 6/025; A61B 6/035; A61B 6/0457; A61B 6/0478; A61B 6/06; A61B 6/145; A61B 6/4476; A61B 6/466; A61B 6/501; A61B 6/547; A61B 6/4441; A61B 6/4435; A61B 6/04; A61B 6/42; A61B 6/4208; A61B 6/5223; A61B 6/588; A61B 2090/3937; A61B 6/0492; A61B 6/52; A61B 6/5294; A61B 6/584; A61B 6/589; G06T 3/0031; G06T 3/0068; G06T 2207/10116; G06T 2207/30036; G06T 7/0028; G06T 7/33; G06K 9/522; G06K 9/6206
USPC .............................. 378/38, 39, 62, 168, 191
See application file for complete search history.

(56) References Cited

U.S. PATENT DOCUMENTS

| | | | |
|---|---|---|---|
| 9,084,568 B2 | 7/2015 | Katsumata | |
| 2007/0041489 A1* | 2/2007 | Siltanen | A61B 6/14 378/4 |
| 2009/0310741 A1* | 12/2009 | Borghese | A61B 5/0064 378/37 |
| 2015/0146853 A1* | 5/2015 | Spartiotis | A61B 6/466 378/62 |
| 2016/0166226 A1* | 6/2016 | Abkai | A61B 6/032 378/63 |
| 2017/0281101 A1* | 10/2017 | Choi, II | A61B 6/461 |

OTHER PUBLICATIONS

German Office Action dated Sep. 11, 2015.
Deserno T M et al: "A posteriori registration and subtraction of panoramic compared with intraoral radiography", Oral Surgery, Oral Medicine, Oral Pathology, Oral Radiology and Endodontics, Mosby-Year Book, St. Louis, MO, US, vol. 108, No. 2, Aug. 1, 2009 (Aug. 1, 2009), pp. e39-e45, XPO26319171, ISSN: 1079-2014, DOI: 10.1016/J. TripleO.2009.03.036 (retrieved on Jul. 15, 2009) p. e40-p. e42.
Mekky N E et al: "A new dental panoramic X-ray image registration technique using hybrid and hierarchical strategies", Computer Engineering and Systems (ICCES), 2010 International Conference On, IEEE, Piscataway, NJ, USA, Nov. 30, 2010 (Nov. 30, 2010), pp. 361-367, XP031840024, ISBN: 978-1-4244-7040-2 abstract.

* cited by examiner

METHOD AND APPARATUS FOR PROVIDING TWO DIGITAL PANORAMIC LAYER IMAGES

TECHNICAL FIELD

The invention relates to a method for providing a first and a second digital panoramic layer image, wherein the two panoramic layer images are respectively generated, in accordance with a computation rule and by forming a panoramic layer, from projections detected during an at least partial revolution of a recording unit around an object to be recorded.

PRIOR ART

In dental x-ray diagnostics, it is often necessary to implement process controls—for example, before/after comparisons, courses of therapy, or growth processes. If such comparisons are based upon digital panoramic layer images, the comparison often turns out to be difficult, since the geometric distribution of tissue structures in the images very critically depends upon the positioning of the patient, and this often cannot be reconstructed with the necessary precision.

The object of the present invention is therefore to provide a method which provides for a comparison of optimized digital panoramic layer images.

DISCLOSURE OF THE INVENTION

This object is achieved via a method for providing a first and a second digital panoramic layer image, wherein, for the first and second panoramic layer images, multiple projections are detected and stored by means of at least one digital detector during an at least partial revolution of a recording unit around an object to be recorded, and the first and second panoramic layer images are each produced from the multiple projections in accordance with a computation rule, wherein a panoramic layer is respectively formed in the generation.

Differences between the first and second panoramic layer images are minimized by altering at least one parameter of the computation rule in case of a new production of the first and/or second panoramic layer image.

Digital panoramic layer images are generated by using CCD or CMOS sensors, for example, which detect x-rays converted into light by means of a scintillator layer, for example. Typically, e.g., in Full Frame Panorama Imaging (FFpan), numerous projections (for example, several thousand individual projections) are generated from different directions and, respectively, individually stored during an at least partial revolution. The superposition of different recording directions, which leads to the formation of the typically sharp layer (referred to here as a panoramic layer) for panoramic layer images, or to the formation of the typically blurred portions, occurs only retroactively in the production of the panoramic layer image, via a corresponding addition of individual projections in accordance with a computation rule.

The result—thus, the panoramic layer image, or the panoramic image, as well as the blurry portions—may thereby be altered by varying parameters of the computation rule. For example, the curve (or the position and the shape) of the panoramic layer in the panoramic layer image to be produced is variable, via change to the addition of the individual projection images. For example, the curve of the sharp layer may be rotationally shifted or rotated by a few millimeters in a translation direction, or in a range of a few degrees, via a corresponding alteration of the computation rule for the production. The shape (for example, the curvature and/or thickness) of the layer may also be altered by a corresponding change to the computation rule for the generation. The shape of the panoramic layer may be modified by a spreading, a compression, or a scaling within the scope of the computation rule, for example.

This leeway with regard to the position or the curve and the shape of the panoramic layer in digital panoramic layer images to be produced is utilized in order to retroactively compensate for, or at least reduce, possible differences in the positioning of a patient for a first and a second digital panoramic layer image.

For this, differences between the two panoramic layer images to be compared are determined and minimized, in that the position or the curve and/or the shape of the panoramic layer is varied in one of the two images, or also in both images, which is achieved by changing the computation rule for the first and/or second panoramic layer image.

If only at least one parameter of the computation rule varies for the first or the second panoramic layer images—thus, if only one of the two panoramic layer images is recalculated—the computation cost is small. For this, a minimization of the difference due to the variation of the panoramic layer for both panoramic layer images possibly enables a better result, and thus a smaller difference in the ultimately obtained panoramic layer images.

The parameter to be changed is advantageously a position and/or a shape of the panoramic layer.

A change in the position and/or the shape (for example, the curvature or the thickness of the panoramic layer) typically enables a reliable minimization in the established differences. For example, after an initialization of the layer shape and layer position, the minimization process may start with a position search, and subsequently implement a correction or alteration of the shape. The two steps may be repeated until a termination criterion is reached, for example.

The position of at least one panoramic layer is, advantageously, modified with regard to three translation and three rotation axes.

The variation with regard to all possible degrees of freedom enables the best result to be obtained with regard to the minimization of differences.

The shape of the panoramic layer is, advantageously, altered by a spreading and/or compression and/or scaling.

Such a change to the shape of the panoramic layer image may, for example, be achieved via a corresponding change to the addition rules for the production of the panoramic layer image. Such a change enables a minimization of differences between the two panoramic layer images—in particular, when the jaw to be measured has changed in size (thus, grown) between the points in time at which the images to be compared were produced.

The differences are advantageously minimized by means of an optimization method.

The use of optimization methods enables a reliable discovery of the optimal, or at least very suitable, position and/or shape of the panoramic layer in the first and/or second panoramic layer image.

The optimization method is, advantageously, a brute force search method, or a gradient method, or a structure search method.

These are examples of especially suitable optimization methods, with the aid of which the optimal position and/or shape of the panoramic layer may be simply determined in the first and/or second panoramic layer image.

The panoramic layer is, advantageously, varied in different ways in at least two different zones of the panoramic layer image.

For example, the position and/or the shape of the panoramic layer may thus be adapted to the conditions of the object. With a measurement of the jaw of a person, the position of the panoramic layer—for example, in the zone of the maxilla—may in this way be adapted to its curve, whereas it may be adapted to its curve in the zone of the mandible [sic].

Furthermore, the invention relates to an apparatus for providing a first and a second digital panoramic layer image. The apparatus comprises a calculation unit, a dental x-ray device having an x-ray source and at least one digital x-ray detector that can respectively be moved at least partially around a recording space, and a means for transferring projections detected with the detector to the calculation unit. The calculation unit is designed to produce the first and second panoramic layer images, respectively from multiple projections detected during a revolution, according to a computation rule and by forming a panoramic layer, and to execute the method described in the preceding.

BRIEF DESCRIPTION OF THE DRAWINGS

The method according to the invention and the apparatus according to the invention are explained using the drawings. Shown are.

EMBODIMENTS OF THE INVENTION

Figure 1:
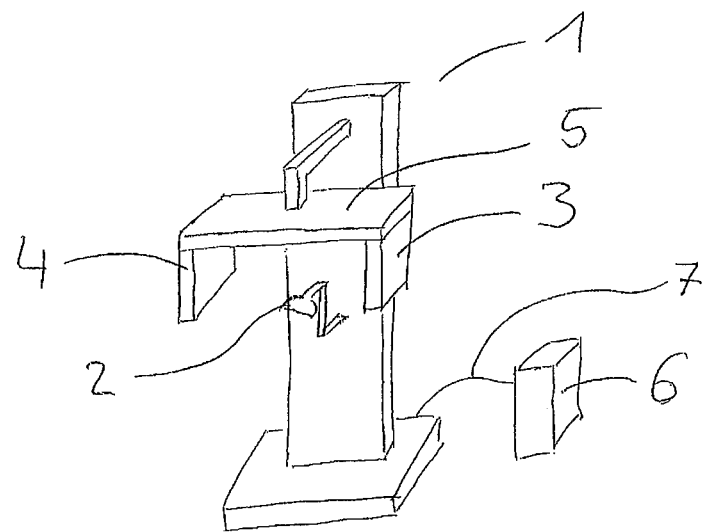
FIG. 1 an apparatus for providing a first and a second digital panoramic layer image.
Figure 2:
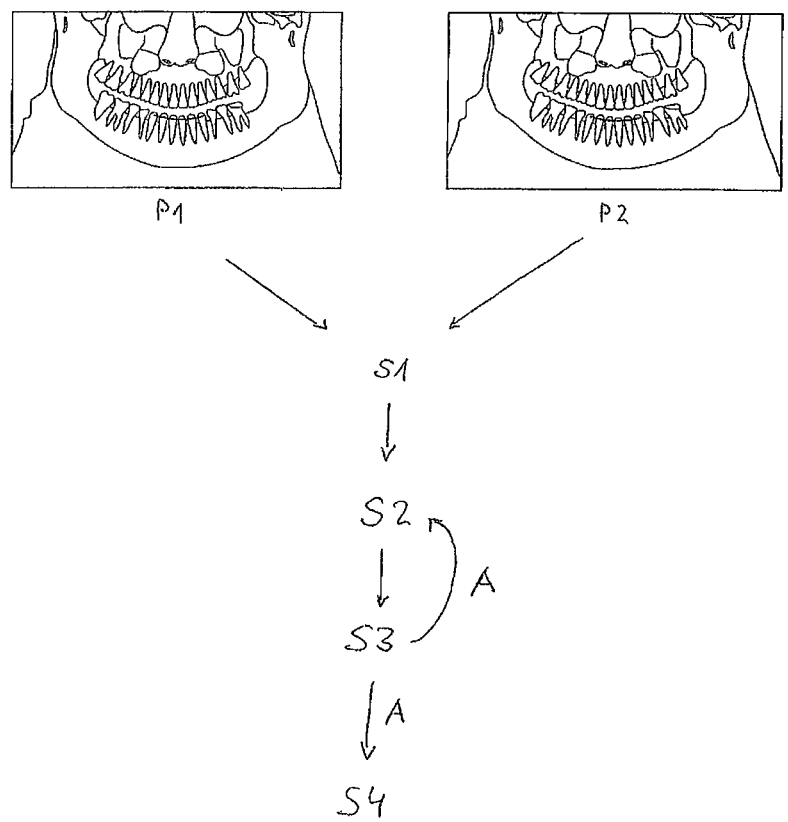
FIG. 2 a method for providing a first and a second digital panoramic layer image.

Drawn in FIG. 1 is a dental x-ray device 1 for producing panoramic layer images P1, P2. A patient is typically positioned by means of a positioning device 2 in a recording space between an x-ray source 3 and at least one digital x-ray detector 4, wherein the x-ray source 3 and the x-ray detector 4 are arranged on a rotatable arm 5 and can be moved in at least partial circles around a recording space and a patient positioned therein, so as to produce a panoramic layer image P1, P2. During this at least partial revolution, a projection is respectively detected by means of the x-ray detector 4 for various angle positions of the arm 5 relative to the positioned patient, and said projection is transmitted to a calculation unit 6 by means of a transmission system 7. 3000 such projections, for example, may be detected during a full revolution.

Following the revolution, a panoramic layer image P1, P2 is produced by means of the calculation unit 6 from the detected projections, in that these are added or superimposed according to a computation rule, so that a classical panoramic layer image results, with a sharp layer (the panoramic layer) and a blurry portion. The more projections that are produced or form the basis for the panoramic layer image, the more distinct the resulting panoramic layer.

In order to monitor a course of growth or therapy, such a digital panoramic layer image of the same patient may be respectively generated at time intervals, for example. At a first point in time, a first panoramic layer image P1 is thus produced from projections produced during a first revolution and, after some time, a second panoramic layer image P2 is produced from projections of the same patient that are produced during a second revolution, wherein the patient should be positioned as identically as possible for both panoramic layer images P1, P2, and, respectively, the same computation rule is used to produce the two panoramic layer images P1, P2 from the respective projections.

In order to further optimize the two panoramic layer images for the comparison, according to the invention, the difference between the panoramic layer images P1, P2 is minimized. Differences which are based only upon a different positioning of the patient or different conditions in the recording should in this way be eliminated as completely as possible, or at least to the extent possible, so that real differences in the object to be recorded (the patient, for example) are more simply and clearly recognizable in the images at the two recording points in time.

For example, for this purpose, differences U1 between the two panoramic layer images P1, P2 are determined in a first step S1, based upon two panoramic layer images P1, P2 produced according to the same computation rule, and by forming a respective panoramic layer from the respective projection images. For example, in a second step S2, the first panoramic layer image P1 is produced again from the projection images detected during the first revolution, wherein a position and/or a shape of the panoramic layer is varied by changing the computation rule. Step S2 may also provide for calculating only the second panoramic layer image P2 again with a modified computation rule, or for producing both panoramic layer images P1, P2 again, with a respectively new computation rule.

In the subsequent step S3, depending upon the selection of step S2, the newly produced first panoramic layer image P1 is compared with the second panoramic layer image P2, or the first panoramic layer image P1 is compared with the newly produced second panoramic layer image P2, or the newly produced first panoramic layer image P1 is compared with the newly produced second panoramic layer image P2, and differences U2 are determined.

Steps S2 and S3 are repeated until the determined difference between the current panoramic layer image P1, P2 is optimally small or is no longer present, or a termination condition A is satisfied.

For example, a limit value for the differences U1, U2 may be provided, and a termination of the minimization may take place as soon as this limit value is underrun. Or, an optimization method for minimizing the differences U1, U2 is used which has a different termination condition.

In the final step S4, the two current panoramic layer images P1, P2 are stored and/or output, in order to provide them to a user for comparison.

The difference between the panoramic layer images P1, P2 may be determined or evaluated by means of a mutual information method, for example. A minimization may then include the following method steps, for example: A first parameter (the position, for example) is varied (via translation, for example). At least one of the two panoramic layer images P1, P2 is re-calculated with the modified parameter. The difference between the re-calculated panoramic layer images P1 and P2, or between the re-calculated and unmodified panoramic layer images P1, P2, is evaluated according to the mutual information method. These steps are repeated until a minimum is reached. A corresponding minimization in the difference is subsequently produced with regard to one or more additional parameters, for example. To minimize the difference, for example, the first parameter is subsequently varied again, then the second parameter, etc., until a general minimum in the difference or a general maximum in the identity has been found or is achieved.

REFERENCE CHARACTERS 1 digital x-ray device
2 positioning device
3 x-ray source
4 x-ray detector
5 rotatable arm
6 calculation unit
7 transmission system
A termination condition
P1 panoramic layer image
P2 panoramic layer image
S1 step 1
S2 step 2
S3 step 3
S4 step 4
U1 differences
U2 differences

The invention claimed is:

1. Method for providing a first and a second digital panoramic layer image, the method comprising;
detecting and storing multiple projections of the first and second panoramic layer images with at least one digital detector during at least one partial revolution of a recording unit around an object to be recorded,
producing the first and second panoramic layer images from the multiple projections in accordance with a computation rule;
forming a panoramic layer for the first and/or second panoramic layer images; and
minimizing differences between the first and second panoramic layer images by:
varying at least one parameter of the computation rule through repeatedly modifying and correcting a position and/or shape of the panoramic layer of the first and/or second panoramic layer images in order to produce new first and/or second panoramic layer images, until a predetermined termination criteria is achieved.

2. Method according to claim 1, wherein the position of the panoramic layer is altered with regard to three translation and three rotation axes.

3. Method according to claim 1, wherein the shape of the panoramic layer is advantageously altered by a spreading and/or compression and/or scaling.

4. Method according to claim 1, wherein the differences are minimized by an optimization method.

5. Method according to claim 4, wherein the optimization method is a brute force method, a gradient method, or a structure search method.

6. Method according claim 1, wherein the panoramic layer is varied in at least two different areas of the panoramic layer image.

7. A device for providing a first and a second digital panoramic layer image, the device comprising a calculation unit, a dental x-ray device having an x-ray source and at least one digital x-ray detector configured to be moved at least partially around a recording space, and means for transmitting projections detected with the detector to the calculation unit, wherein the calculation unit is designed to produce the first and second panoramic layer images respectively from multiple projections detected during a revolution, according to a computation rule and with formation of a panoramic layer, wherein the calculation unit is configured to execute the method according to claim 1.

* * * * *